United States Patent [19]

Lower et al.

[11] Patent Number: 4,797,204

[45] Date of Patent: Jan. 10, 1989

[54] AUTOMATIC PARTICLE-SIZE ANALYZER WITH DIVIDED DRUM

[75] Inventors: William E. Lower; Glenn J. Pogue, both of Cincinnati, Ohio

[73] Assignee: Rotex, Inc., Cincinnati, Ohio

[21] Appl. No.: 167,959

[22] Filed: Mar. 14, 1988

[51] Int. Cl.[4] .............................................. B07B 1/28
[52] U.S. Cl. ................................. 209/237; 209/261; 209/287; 209/309; 209/311
[58] Field of Search .............. 209/237, 239, 284, 287, 209/288, 289, 290, 309, 311, 400, 407, 235, 659, 680, 683, 261

[56] References Cited

U.S. PATENT DOCUMENTS

| | | | |
|---|---|---|---|
| 1,798,459 | 3/1931 | Elmore et al. | 209/290 |
| 3,591,001 | 7/1971 | Quesnel | 209/407 X |
| 3,750,884 | 8/1973 | Satake | 209/683 X |
| 4,043,901 | 8/1977 | Gauld | 209/683 X |
| 4,487,323 | 12/1984 | Marrs | 209/683 |
| 4,702,826 | 10/1987 | Pogue | 209/237 |

FOREIGN PATENT DOCUMENTS 976004 11/1964 United Kingdom ............... 209/289

Primary Examiner—Johnny D. Cherry
Assistant Examiner—Donald T. Hajec
Attorney, Agent, or Firm—Wood, Herron & Evans

[57] ABSTRACT

An apparatus for automatic screen analysis of a granular material in which the material is screened from a polygonal drum which is divided crosswise into at least two chambers by a transverse partition. A first chamber has progressively coarser screens on each of its faces except one, which has a downward slanting ramp for transferring the sample into a second chamber. Particles are transferred or chuted into the second chamber after they have been screened on all the screens of the first chamber. The second chamber has screens progressively coarser than those in the first chamber, for making more cuts. This construction increases the number of graded screening surfaces available without requiring greater drum length or more sides.

15 Claims, 3 Drawing Sheets

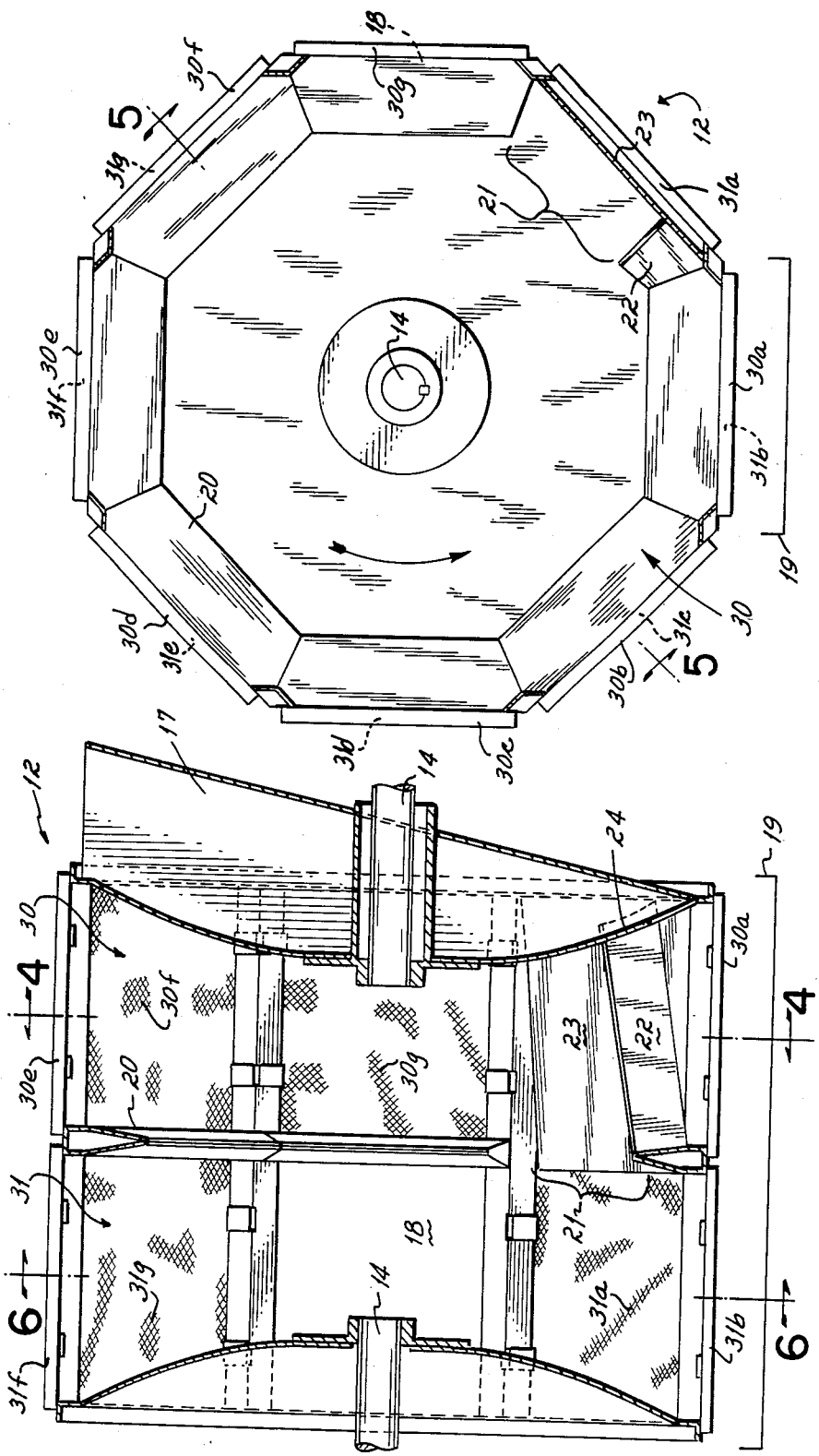

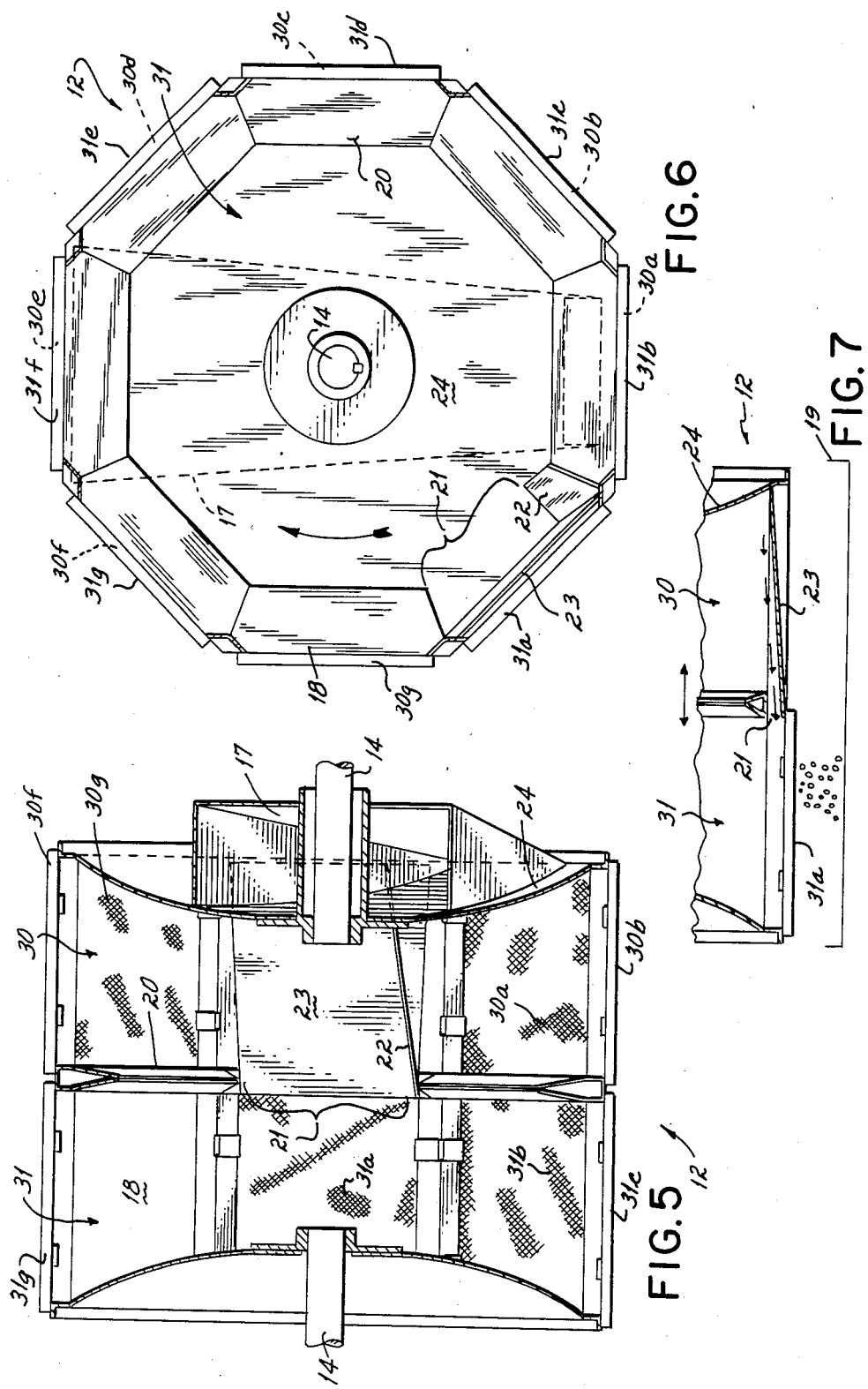

AUTOMATIC PARTICLE-SIZE ANALYZER WITH DIVIDED DRUM

FIELD OF THE INVENTION

This invention relates to automatic particle-size analyzers for separating particulate samples into defined particle size ranges. More specifically, the invention relates to analyzers of the type having a polygonal drum with graduated screens on its faces.

DESCRIPTION OF THE PRIOR ART

Particle-size analysis is a standard industrial test which is used on a wide variety of materials. Many bulk particulate items of commerce are sold according to some predetermined particle size requirement or classification. In addition, size classification data is frequently used as a control in various manufacturing processes. Such classification is usually referred to as a screen analysis, a term chosen from the laboratory method of determining the particle size distribution of a sample. Heretofore, a common method of running a screen analysis has been to assemble a stack of graduated screens in which the uppermost screen is the coarsest and lowermost screen is the finest in terms of mesh size. The sample to be analyzed is placed on the top screen and the entire stack of screens is shaken or vibrated in a screening motion. The material remaining on each screen and on the bottom pan is weighed separately and those weights are used to calculate a particle size analysis which is usually expressed in terms of the weight percent of the sample which is retained on the respective screens of the stack.

A common industrial screening device employs an inclined rotary drum. The drum surface is made of screens which are graduated along its length, from relatively fine at the entrance end to relatively coarse at the discharge end. In this type of apparatus the various fractions fall into separate bins or are carried away on different conveyor systems to be weighed. Both the stacked screen analyzers and the inclined rotary drum devices generally require manual weighing and calculation to determine the particle size analysis.

An automatically operating size analyzer having an indexing polygonal drum is disclosed in Marrs U.S. Pat. No. 4,487,323, which disclosure is incorporated herein by reference. In Marrs the polygonal drum has graded screens on its different circumferential faces. The screens are successively positioned in a horizontal screening position by rotationally indexing the drum in increments about its axis. The drum is shaken so that the sample is screened on each screen while in the screening position. The Marrs apparatus includes a means for automatically weighing each size fraction and calculating the size analysis of the sample.

The Marrs apparatus is inherently limited by the practical maximum of the number of different faces and screening surfaces which can be provided on the drum. Inherently, the more cuts desired, the greater the number of graded screening surfaces required. However, if the drum has too many faces, the angle between adjacent faces is so oblique that particles will spill from the face at the screening position, onto adjacent screens, which could distort the analysis. Typically the drum will have six or eight faces and can make five or seven separate cuts (one face is usually left open, for loading and for dumping oversize particles). Where a greater number of cuts is desired, it is necessary either to use an additional screener having a drum with different screen sizes, or to change screens on the analyzer and run the sample again.

There has been a need for an automatic particle-size analyzer which can separate a sample into a greater number of size ranges than has heretofore been possible, without correspondingly increasing the size, complexity and cost of the analyzer.

SUMMARY OF THE INVENTION

The present invention is an improvement in the general type of polygonal drum automatic particle-size analyzers shown in Marrs. The improvement can increase by twofold or more the number of graded screening surfaces in the analyzer without necessarily making the drum longer or with more sides.

In accordance with the invention, the drum (which can be of the general type shown in Marrs) is divided transversely by a central partition which in effect defines two axially "shorter" screening sections or chambers. The material to be analyzed is charged into one drum half—the first screening chamber—as through a feed chute. The first chamber has progressively coarser screens on each of its faces except one, which has an internal ramp or slanted plate in place of a screen. The ramp slants downwardly (when the ramp is at the screening position), from the end wall of the chamber, toward an opening in the central partition. (As used herein, the terms "screening position" or "down position" are used to mean the downwardmost horizontal position of each screen, to which it is indexed for screening.) A screening motion, which preferably includes a longitudinal component of motion, is applied to the drum as by a gear motor and crank arrangement, which shakes the drum axially. After the sample has been screened for predetermined intervals on each of the screening surfaces of the first chamber, the ramp face is indexed last to the screening position, and the remaining sample tumbles and slides onto the ramp. Under the screening motion, the ramp advances or conveys the particles toward an opening in the central partition longitudinally aligned with the ramp. The sample is conveyed down the ramp from the first chamber through the opening and into the second chamber. The second screening chamber has screens further progressively coarser than those in the first chamber, and once the material sample has been transferred into the second chamber it is screened successively on each of those screens. The last drum face to be indexed to the down position in the second chamber may be open and acts as a discharge port for any sample material larger than the largest screen mesh. By this means the sample material can, for example, be sized into ten progressively graded fractions in an apparatus which otherwise could split it into only five different size fractions.

In a preferred form, the drum partition is a wall which, except for the opening therein adjacent to the ramp, extends substantially circumferentially around the interior surface of the drum. The partition may, but need not necessarily, extend inwardly all the way to the axis of the drum. The ramp preferably has a barrier along one longitudinal edge, which extends from the opening in the partition toward or to the end wall and which longitudinally separates the ramp from the first (finest) screening surface, thereby preventing feedback or reverse flow of material back through the opening and off the ramp after the sample has been transferred into the second chamber.

The objects and advantages of this invention will become further apparent to those skilled in the art upon reading the detailed description in conjunction with the drawings.

DESCRIPTION OF THE DRAWINGS

FIG. 3 is an enlarged axial section through the divided drum, taken on line 3—3 of FIG. 2.

FIG. 4 is a transverse section of the drum, taken on line 4—4 of FIG. 3.

FIG. 5 is an axial section of the drum, taken on line 5—5 of FIG. 4.

FIG. 6. is a transverse section of the drum, taken on line 6—6 of FIG. 3.

FIG. 7 is an enlarged section of the ramp portion of FIG. 3 and diagrammatically shows the flow of sample material from the first chamber into the second chamber.

DETAILED DESCRIPTION OF THE PREFERRED EMBODIMENT

Figures 1, 2:
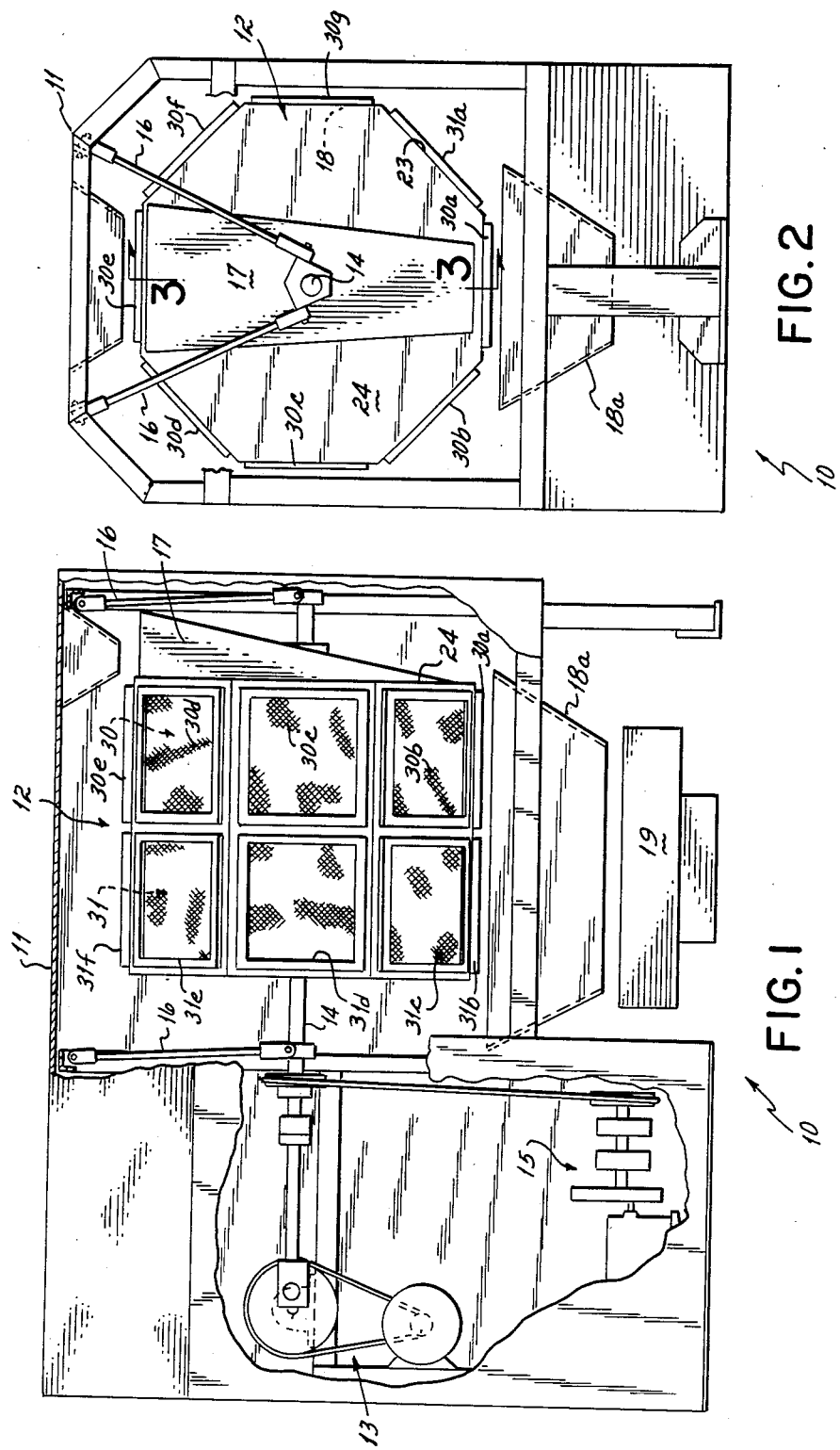
FIG. 1 is a front elevation, partially cut away, of a particle-size analyzer having a divided drum in accordance with a preferred embodiment of the invention.
FIG. 2 is an end elevation of the analyzer.

A divided-drum automatic particle-size analyzer in accordance with a preferred embodiment of this invention is designated at 10 in the drawings. Like Marrs, the divided drum 12 of analyzer 10 shown in the drawings has an octagonal crossection, however, it will be appreciated by those skilled in the art that drums with other polygonal crossections may be used.

Referring to FIGS. 1 and 2, the divided-drum 12 is shown in its preferred operational environment. The automatic particle-size analyzer is housed within an outer housing 11, and has as its main components the divided-drum 12; a gear motor and crank arrangement 13 for applying a longitudinal screening motion to divided-drum 12 by means of shaft 14, to which drum 12 is keyed for movement; a motor drive 15 which rotationally indexes drum 12 about the axis of shaft 14; suspension rods 16 which are pivotally attached at their upper ends to housing 11 and pivotally attached at their lower ends to shaft 14 thereby suspending and journaling drum 12 for longitudinal screening motion; a feed chute 17 for charging particles endwise into the drum; a discharge chute 18a through which all screened particles pass; a weigh pan 19 for weighing particulate matter passing through the screens; and a microprocessor control unit, not shown, which controls screening motor 13 and indexing motor 15 and which automatically calculates the particle size analysis. Reference may be had to the Marrs patent for further description of such embodiment FIGS. 3-7 show a preferred form of divided drum. Drum 12 is divided transversely by a short (low) internal partition or wall 20 which, except for an opening 21 therein, extends substantially circumferentially about the interior surface of drum 12. The partition 20 essentially defines two "shorter" screening segments or chambers—a first screening chamber 30 and a second screening chamber 31. The first chamber 30 is adjacent to feed chute 17 and usually has progressively coarser screens on each of its faces except one. That face has an internal ramp or slanted plate 23 in place of a screen. Ramp 23 slants outwardly (downwardly, when ramp 23 is at the screening position) from end wall 24 of drum 12, toward opening 21 in wall 20. The ramp closes what would otherwise be an open face of the drum. Ramp 23 has an upstanding (as seen in FIG. 3) barrier 22 which extends from opening 21 in partition 20 to end wall 24, this barrier 22 is at an angle to the longitudinal axis of the drum and separates ramp 23 from the first screening surface 30a, thereby preventing reverse flow of the sample material, after the material has been transferred into the second chamber. The second chamber 31 usually has screens further progressively coarser than those in the first chamber 30, on each of its faces except one. That face may be open discharge port 18 and when it is in the down position it discharges any sample material larger than the largest screen mesh, onto collection tray 19.

In FIGS. 3 and 4, divided drum 12 is shown in the initial screening position, that is, with the first (finest mesh) screening face 30a in the down position directly over collecting tray 19. In this position, the particulate sample is fed through feed chute 17 onto the first screening face 30a. The screening motor 13, controlled by the microprocessor unit, applies a longitudinal screening motion for a predetermined period of time during which the particles smaller than the screen openings of the first screening face 30a fall through onto collection tray 19 and their weight is recorded. After a predetermined screening time the indexing motor 15, controlled by the microprocessor, indexes drum 12 (counterclockwise in FIG. 4) so that the second screening face 30b, which has screen openings larger than those in screen 30a, is in the down, screening position. position. The remaining particle sample falls from the first screening face 30a onto the second screening face 30b. Again, the screening motor 13 applies a longitudinal screening motion to the divided drum 12 and particles smaller than the screen openings in the second screening face 30b fall onto the collection tray 19 and their weight is recorded. This process continues until each respective screening face 30a-30g has been indexed to the down screening position. The screen openings in screen faces 30a-30g are progressively larger from the smallest in screen 30a to the largest in screen 30g.

The final indexing of the divided drum 12 in its rotary cycle positions ramp 23 in the down position. Under the screening movement the slope of the ramp transfers or conveys particulate matter on the ramp into the second screening chamber 31, as shown in FIG. 7, and onto the first screening face 31a thereof, which has screen openings larger than those in screen 30g. The particle sample is next screened on the (first screening face 31a in the second chamber 31 by the screening motion, and particles smaller than the screen openings in the first screening face 31a fall through and are collected and weighed. Then indexing motor 15 indexes the divided drum 12 as shown in FIG. 6 such that the second screening face 31b of the second chamber 31 is in the down screening position. The wall 22 along the edge of ramp 23 adjacent screening face 30a prevents feedback or reverse flow of the particle sample into the first chamber 30, during indexing to and screening on screen 31b. As before, drum 12 is indexed by indexing motor 15 such that the particle sample is screened on screens 31a-31g, which have screen openings larger from 31a (smallest, although larger than those in screen 30g of the first chamber) to 31g (largest). Accordingly, the weight of particles that pass through each screen and onto tray 19 is recorded. Any particles remaining on screen 31g, i.e., oversized particles, are discharged from the drum onto tray 19 through discharge port 18 when it is indexed to the down position. When the above-described process has been completed, the particle size analysis is automatically calculated and printed out, in a manner known per se.

It should be noted that the invention contemplates use of two or more screens of the same size on adjacent faces of the drum, or even in different chambers, if desired, as for example where fewer cuts than the maximum are needed. Similarly, the microprocessor may optionally be programmed to "skip," or index past, one or more screens, if not needed for a particular type of sample. The microprocessor can index screens in any desired sequence. Moreover, the invention contemplates various means other than a ramp for transferring the sample material from the first screening chamber into the second screening chamber; for example, a motor driven conveyor belt, a blower, or a manual transfer. The invention further contemplates dividing the drum into more than two screening chambers.

While the preceding description includes the best mode known to the inventor of practicing the present invention, it will be appreciated by those skilled in the art that variations on it are possible. Thus, the scope of the invention should be considered to be limited only in accordance with the following claims.

What is claimed is:

1. In a particle size analyzer of the type having a hollow polygonal drum with a plurality of faces on its periphery with graded screens on different faces thereof, means for rotationally indexing said drum about its longitudinal axis to sequentially position each face in a generally horizontal screening position, and means for applying a screening motion to said drum while in said screening position the improvement comprising:
    a. partition means within said drum, said partition means transverse to said longitudinal axis and dividing said drum into first and second screening chambers,
    b. said drum having screens of different mesh sizes on the respective faces of said first and second chambers,
    c. means for feeding the material to be analyzed into said first chamber,
    d. means for transferring said material from said first chamber into said second chamber.

2. The improvement of claim 1 wherein said transferring means is an internal ramp in said first chamber on a face thereof which receives said material when the face having said transferring means is indexed to a screening position, said ramp in said screening position slanting toward said partition means to direct said material when said screening motion is applied.

3. The improvement of claim 2 wherein said partition means presents an opening between said chambers, said opening aligned longitudinally with said ramp to permit said material on said ramp to be transferred by the screening motion from said first chamber into said second chamber through said opening when said transfer face is indexed to the screening position and said screening motion is applied.

4. The improvement of claim 3 wherein said ramp extends generally parallel to the longitudinal axis of said drum, from an end wall of said drum toward said opening.

5. The improvement of claim 3 wherein said screens are arranged progressively within said first chamber such that each screening face has larger screen openings than the prior screening face when said drum is rotationally indexed.

6. The improvement of claim 5 wherein said screens are arranged progressively within said second chamber such that each screening face has larger screen openings than the prior screening face when said drum is rotationally indexed.

7. The improvement of claim 6 wherein the smallest screen opening size in a screening surface in the second chamber is larger than the largest screen opening size in a screening surface in said first chamber.

8. The improvement of claim 3 further comprising:
    e. a wall extending along said ramp from a point on said partition means adjacent said opening, said wall forming a barrier along an edge of said ramp at an angle to the longitudinal axis of said drum to block return of material back to screens of said first chamber after transfer into said second chamber.

9. The improvement of claim 8 wherein said wall generally separates said ramp from a first screening face, said first screening face having the smallest screen openings of all of said screening faces.

10. The improvement of claim 1 wherein said partition means is a wall extending in the circumferential direction about the interior surface of said drum, but not extending to the axis of the drum.

11. The improvement of claim 9 wherein said wall extends at an oblique angle from said partition.

12. The improvement of claim 1 wherein said screening motion shakes said drum back and forth generally along its longitudinal axis.

13. In the method of making a particle size analysis wherein a particulate sample is placed in a polygonal drum having a plurality of faces on its periphery with different size openings on different faces thereof, the drum is indexed to first present the finest mesh screen at a generally horizontal screening position and the sample is screened at such position, and the drum is indexed thereafter to present screens of progressively larger size openings at the screening position, the improvement comprising:
    (a) dividing the drum transversely with a partition to define longitudinally separated first and second screening chambers therein,
    (b) providing a first set of screens on the faces of said drum in said first chamber,
    (c) providing a second set of screens on the faces of said drum in said second chamber, said second set of screens having openings therein coarser than those of said first set of screens,
    (d) charging the sample into said first screening chamber and confining it therein while screening it on said first set of screens,
    (e) after the sample has been screened on one or more of said first set of screens in said first chamber, transferring the sample longitudinally through said partition from said first chamber into said second chamber,
    (f) then screening the sample on one or more of said second set of screens in said second chamber.

14. The method of claim 13 wherein said transferring is accomplished by providing an opening in said partition;
    indexing the drum so that said opening is at the screening position; and applying a longitudinal motion to the drum to convey the sample through said opening into said second chamber.

15. The method of claim 14 wherein said sample is deposited on a ramp in said first chamber, which slants toward second opening, and said particles are conveyed by sliding down said ramp.

* * * * *